US006958079B1

(12) United States Patent  (10) Patent No.: US 6,958,079 B1
Taylor et al.  (45) Date of Patent: Oct. 25, 2005

(54) PERORALLY INSERTABLE/REMOVABLE ANTI-REFLUX VALVE

(75) Inventors: Thomas V. Taylor, Houston, TX (US); Frank G. Weeden, Houston, TX (US)

(73) Assignee: Reflux Corporation, Houston, TX (US)

( * ) Notice: Subject to any disclaimer, the term of this patent is extended or adjusted under 35 U.S.C. 154(b) by 58 days.

(21) Appl. No.: 10/064,324

(22) Filed: Jul. 2, 2002

Related U.S. Application Data

(60) Provisional application No. 60/302,870, filed on Jul. 3, 2001.

(51) Int. Cl.[7] .............................................. A61F 2/04
(52) U.S. Cl. ................................................ 623/23.68
(58) Field of Search ........................... 623/23.68, 1.24, 623/1.28, 2.12, 2.13, 2.14, 2.15, 2.16, 2.17, 623/2.18, 2.19, 1.36

(56) References Cited

U.S. PATENT DOCUMENTS 5,855,601 A * 1/1999 Bessler et al. ............. 623/2.38
6,558,429 B2 * 5/2003 Taylor ...................... 623/23.68

6,676,698 B2 * 1/2004 McGuckin et al. ........ 623/1.24

* cited by examiner

Primary Examiner—Bruce E. Snow
(74) Attorney, Agent, or Firm—Daniel N. Lundeen; Lundeen & Dickinson, LLP (57) ABSTRACT

Disclosed are esophageal anti-reflux valve prostheses, and tools and procedures for peroral implantation and extraction of the prostheses. The prostheses disclosed have a semipermeable membrane to allow retrograde passage of gas, magnets disposed at a distal end of the sleeve to facilitate closure, and an outwardly bendable array of spikes that are longitudinally aligned for peroral insertion and lockable into a radially outwardly deployed configuration to keep the prosthesis from dislocating implantation. The implantation tool has inner and outer concentric tubes, the inner tube releasably threadably connected to the prosthesis, the outer tube reverse threaded with the inner tube to advance a distal headpiece to engage, deploy and lock the spikes into the deployed configuration. A vacuum assist can be used to help impact the lumen wall on the spikes. The extraction tool is similar to the implantation tool with an inner tube for threadably engaging the prosthesis, an outer tube with a distal crown with a plurality of shoes to unseat and unlock the spikes, and an overtube shield to receive the spikes and facilitate extraction of the prosthesis.

45 Claims, 10 Drawing Sheets

PERORALLY INSERTABLE/REMOVABLE ANTI-REFLUX VALVE

CROSS REFERENCE TO RELATED APPLICATIONS

The present application claims the benefit of U.S. application Ser. No. 60/302,870, filed Jul. 3, 2001, and entitled Perorally Insertable/Removable Anti-Reflux Valve, which is hereby incorporated by reference in its entirety.

BACKGROUND OF INVENTION

This invention relates to a device and non-invasive surgical method for treating gastroesophageal reflux disease. More specifically, it relates to an anti-reflux valve prosthesis and associated instrumentation for its peroral placement and in situ fixing at the gastroesophageal junction, to prevent the reflux of gastric contents into the esophagus. The invention further relates to the instrumentation and methodology for peroral removal of such a prosthesis.

Gastroesophageal reflux disease (GERD) is the commonest cause of dyspepsia, affecting some 30% of the United States adult population intermittently and some 10% on a continuous and troublesome basis. Gastroesophageal reflux disease produces heartburn, abdominal pain and regurgitation of acid-containing gastric contents into the esophagus and pharynx. It may also lead to alteration of the lining of the esophagus (Barrett's Esophagus), which may in turn lead to esophageal cancer. Current methods of treating GERD include powerful antacid medication therapies and surgical interventions.

Medication therapy with powerful antacids is directed at treating the symptoms of GERD, and is necessarily not curative. Furthermore, medication-based therapies are not always fully effective, as reflux is not prevented and the esophagus may continue to be exposed to gastric content.

Surgical intervention typically involves either open surgery (performed through the abdomen or the chest) or laparoscopic surgery (performed through one or more incision access ports inserted through the abdominal wall), and the re-sectioning of tissue or the implanting of a prosthetic device. Although surgical interventions can be curative, these treatments are seriously invasive and have the attendant risk of such procedures. Despite the risk, the field has been motivated to provide solutions to the GERD problem, which has resulted in the development of a number of surgically implantable anti-reflux valve prosthetic devices. Prior anti-reflux valve prostheses are essentially one-way valves implanted at the gastroesophageal junction using open or laparoscopic surgery. The implanted prosthesis allows normal swallowing to take place in an orthograde manner while preventing the reflux of gastric contents from the stomach into the esophagus.

Examples of surgically implanted esophageal anti-reflux valve prostheses include the devices of: Godin (U.S. Pat. No. 5,314,473) which discloses a one-way, antivalve comprising a flattened tubular part associated with an annular fixing element; and Reich (U.S. Pat. No. 4,846,836) which discloses a bi-directional valve and housing for similar purposes. These devices were developed to be inserted into the gastroesophageal junction via open or laparoscopic surgery and fixed there. The purpose was to permit the unidirectional passage of ingested materials into the stomach while preventing the reflux of gastric content of the stomach into the esophagus. Typically, these devices require suturing or other means to fix them to the tissue of the esophagus.

Generally, all of these prior devices and methods require surgical invasion of a body cavity and breach of the body membrane in some fashion (e.g., open surgery or laparoscopy) in order to accomplish their utility. Invasive surgical interventions are too frequently complicated by problems such as stricture formation, "gas bloat," or recurrent symptoms of reflux disease. Additionally, the results obtained by gross surgical treatment can be technique-dependent and vary significantly from surgeon to surgeon.

More recently, perorally implantable valve prostheses were disclosed for fixation in the esophageal lumen near the gastroesophageal junction in patent applications by one of the present co-inventors, Dr. Thomas V. Taylor, U.S. Ser. No. 08/987,693, filed Dec. 9, 1997, U.S. Pat. No. 6,254,642; U.S. Ser. No. 09/681,364, filed Mar. 26, 2001, U.S. Pat. No. 6,544,291; and U.S. Ser. No. 09/681,364, filed Mar. 26, 2001, U.S. Pat. No. 6,544,291; each of which is hereby incorporated herein by reference in its entirety.

SUMMARY OF INVENTION

The present invention relates to an anti-reflux valve prosthesis system for treating gastroesophageal reflux disease (GERD) in a patient, which does not require open or laparoscopic surgery to implant. The present invention provides for perorally inserting a removable sutureless anti-reflux valve prosthesis down the lumen of the esophagus, to the gastroesophageal junction, where it is fixed in place. The advantage of this system is that peroral insertion of such a valve eliminates the need for either open formal laparotomy, thoracotomy or a laparoscopic approach using multiple access ports. In the event it is later desired to remove or replace the prosthesis, the valve can be removed using a peroral extraction tool, again generally without the need for laparotomy, thoracotomy, laparoscopy, or any other surgically invasive technique.

In one aspect, the present invention provides an anti-reflux valve prosthesis. The prosthesis has an annular fixation element for fixing the prosthesis in an esophagus, and a one-way valve depending from the annular fixation element for allowing orthograde passage therethrough and inhibiting retrograde passage of gastric contents. The valve includes a semipermeable membrane that is essentially liquid impermeable, but gas permeable to allow retrograde permeation of gas through the valve. The prosthesis can be configured to be perorally installed or perorally removable. The one-way valve of the prosthesis can be a sleeve valve. The prosthesis can be made of a biologically inert material, including but not limited to, a fluorinated polymer. The prosthesis is configured to be implanted in the esophagus of a patient with gastroesophageal reflux disease (GERD), preferably when that patient's esophagus is cancer free.

In another aspect, the present invention provides another embodiment of an anti-reflux valve prosthesis that has an annular fixation element for fixing the prosthesis in the esophagus and a sleeve valve depending from the annular fixation element for allowing orthograde passage therethrough and inhibiting retrograde passage of gastric contents. The sleeve valve has a plurality of magnets secured at a distal end thereof to facilitate closure of the valve. Additionally, the prosthesis may contain a gas permeable membrane to allow retrograde permeation of gas therethrough, where the membrane is preferably liquid impermeable.

In still another aspect, the present invention provides an anti-reflux valve prosthesis for peroral implantation in the esophagus. The prosthesis in this embodiment includes an annular body and a valve depending from the annular body for allowing orthograde passage therethrough and inhibiting retrograde passage of gastric contents. A plurality of substantially rigid spikes are spaced along a circumference of the annular body adjacent one end thereof, preferably the proximal end. The valve depending from the annular body can be a sleeve valve which may include a plurality of magnets secured at a distal end to facilitate closure of the valve. The prosthesis may also include a gas permeable, and preferably liquid impermeable, membrane to allow retrograde permeation of gas therethrough. Each spike has a tip at a free end thereof and a base at the other end attached to the annular body. A dog is formed on each spike between the base and the tip. Each spike is outwardly bendable at the base between a retracted generally longitudinal alignment for insertion and a radially outwardly deployed alignment for fixation. Preferably, the spikes can include a chamfer at the base to facilitate the bending. A keeper is positioned on an exterior surface of the annular body for receiving the dogs and locking the respective spike in the deployed alignment. The annular body of the prosthesis can be threaded to allow engagement with a tool to perorally insert and/or remove the prosthesis from the esophagus. The prosthesis is configured to be implanted in the esophagus of a patient with gastroesophageal reflux disease (GERD), preferably when that patient's esophagus is cancer free.

In a further aspect, the present invention provides a tool for implanting the perorally implantable prosthesis. In this embodiment, the annular body is internally threaded and the spikes are attached to a proximal end of the annular body. The tool includes inner and outer tubes, a nipple secured to a distal end of the inner tube for releasably coupling the annular body, and a handle secured adjacent to a proximal end of the inner tube for manipulation of the tool. The inner tube and the outer tube are configured for advancement of the outer tube by rotating the outer tube with respect to the inner tube. A headpiece is secured to a distal end of the outer tube for bending the spikes outwardly into the deployed alignment by advancement of the headpiece into abutment with the nipple. A handle is preferably secured adjacent to a proximal end of the outer tube to facilitate rotation of the outer tube with respect to the first tube. Optionally, a plurality of transverse passages are formed in the headpiece in fluid communication with an annular space defined by an inner diameter of the headpiece, an outer diameter of the inner tube and annular seals on each end thereof. If present, the annular space is in turn in fluid communication with a vacuum source via a transverse bore in a wall of the inner tube and a central longitudinal passage through the inner tube, for drawing a lumen of the esophagus inwardly to facilitate penetration of the spikes. Optionally, a fiber optic cable is disposed within a central longitudinal passage of the inner tube for viewing the esophagus.

In still another aspect of the invention, there is provided a method of using a tool to perorally implant an anti-reflux prosthesis in an esophagus. The method includes: (a) mounting the anti-reflux valve prosthesis onto a headpiece of the tool; (b) positioning the anti-reflux valve prosthesis in the esophagus; (c) deploying a plurality of radial spikes of the prosthesis; (d) pulling a vacuum across a longitudinal passage of the tool; and (e) drawing a lumen of the esophagus inwardly to facilitate impaction of the spikes. Optionally the headpiece of the tool can be configured to be removable and replaced with a crown. The crown would be configured to assist in the peroral removal of the prosthesis from the esophagus.

In still another aspect of the invention, there is provided a tool to perorally implant an anti-reflux prosthesis in an esophagus. The tool includes: (a) a means for mounting the anti reflux valve prosthesis onto a headpiece of the tool; (b) a means for positioning the anti-reflux valve prosthesis in the esophagus; (c) a means for deploying a plurality of radial spikes of the prosthesis; (d) a means for pulling a vacuum across a longitudinal passage of the tool; and (e) a means for drawing a lumen of the esophagus inwardly to facilitate impaction of the spikes.

In still another aspect of the invention, there is provided a method of using a tool for implanting the anti-reflux valve prosthesis. The method includes: (a) perorally inserting and positioning the anti-reflux valve prosthesis into the esophagus; (b) deploying a plurality of spikes, the spikes depending radially from the anti-reflux prosthesis; and (c) impaling the esophagus upon the spikes to hold the prosthesis in place. Optionally, the method can include using a vacuum to assist in impaling the esophagus upon the spikes.

Furthermore, another aspect of the invention provides for a tool to implant an anti-reflex prosthesis. The tool includes: (a) a means for perorally inserting and positioning the anti-reflux valve prosthesis into the esophagus; (b) a means for deploying a plurality of spikes, the spikes depending radially from the anti-reflux prosthesis; and (c) a means for penetrating the esophagus with the spikes to hold the prosthesis in place.

In still another aspect of the invention, there is provided a method of using a tool for implanting an anti-reflux valve prosthesis. The method includes: (a) releasably engaging a nipple of the tool with an annular body of the prosthesis, the prosthesis having a plurality of retractable embedment spikes; (b) perorally inserting the valve prosthesis into the esophagus near the gastroesophageal junction; (c) extending the spikes fully outwardly into a deployed alignment for engagement with a lumen of the esophagus; (d) uncoupling the nipple from the prosthesis; and (e) withdrawing the tool from the esophagus. Furthermore, the method can optionally include actuating a vacuum source to draw the wall of the lumen inwardly and facilitate engagement of the spikes.

In still another aspect of the invention, there is provided a tool for implanting an anti-reflux valve prosthesis. The tool includes: (a) a means for releasably engaging a nipple of the tool with an annular body of the prosthesis, the prosthesis having a plurality of retractable embedment spikes; (b) a means for perorally inserting the valve prosthesis into the esophagus near the gastroesophageal junction; (c) a means for extending the spikes fully outwardly into a deployed alignment for engagement with a lumen of the esophagus; (d) a means for uncoupling the nipple from the prosthesis; and (e) a means for withdrawing the tool from the esophagus.

A further aspect is the provision of a tool for extracting the anti-reflux prosthesis wherein the prosthesis includes an annular body and extended radial spikes therefrom. The tool includes an inner tube and an outer tubes, with the tubes being generally concentrically aligned, an nipple secured to a distal end of the inner tube, the nipple configured to be releasably coupled with the annular body, and a crown secured to a distal end of the outer tube, the crown having a plurality of tangentially projecting shoes to receive and retract the extended radial spikes. Optionally, the outer tube of the tool can be configured to be advanced or retracted as the outer tube is rotated with respect to the inner tube. The tool can also comprise a handle secured to a proximal end of the inner tube for manipulation thereof. The tool can also include a second handle secured adjacent to a proximal end of the outer tube to facilitate movement of the outer tube with respect to the inner tube. The tool can optionally include a fiber optic cable disposed within a central longitudinal passage of the inner tube for viewing the esophagus. The tool can optionally include an overtube having a shield of enlarged diameter at a distal end thereof, wherein the overtube is slidable over the outer tube to receive the plurality of spikes to facilitate removal of the prosthesis from the esophagus. The shield may optionally be tapered from a larger diameter at a distal end to a smaller diameter at a proximal end. The crown may optionally be configured to be removable and replaced with a headpiece that is configured to assist in reinstalling the prosthesis into the esophagus.

A further aspect of the invention involves a method for using a tool to extract an anti-reflux valve prosthesis from an esophagus. The method includes: (a) perorally inserting the tool into the esophagus, wherein the tool comprises a nipple and a crown; (b) engaging the nipple into an annular body of the prosthesis, wherein the prosthesis includes a plurality of extended embedment spikes; (c) advancing the crown with respect to the nipple, the crown configured to retract the embedment spikes; and (e) removing the tool and engaged prosthesis from the esophagus. Optionally, the method can include advancing a shield over the spikes to place the spikes into a retracted position.

A further aspect of the invention involves a tool to extract an anti-reflux valve prosthesis from an esophagus. The tool includes: (a) a means for perorally inserting the tool into the esophagus, wherein the tool comprises a nipple and a crown; (b) a means for engaging the nipple into an annular body of the prosthesis, wherein the prosthesis includes a plurality of extended embedment spikes; (c) a means for advancing the crown with respect to the nipple, the crown configured to retract the embedment spikes; and (e) a means for removing the tool and prosthesis from the esophagus. Optionally, the tool can include means for advancing a shield over the spikes to place the spikes into a retracted position.

An alternate embodiment of the invention is an anti-reflux valve prosthesis for peroral implantation in the esophagus, comprising an annular body preferably made of a biologically inert polymer, a valve depending from the annular body for allowing orthograde passage therethrough and inhibiting retrograde passage of gastric contents, and a plurality of substantially rigid spikes spaced along a circumference of the annular body adjacent one end thereof and extending radially outwardly from the annular body. Each spike has a tip at a free end thereof and a base at the other end attached to the annular body. Each spike is temporarily inwardly bendable for implantation and has memory to return to the radially outwardly extending position.

Another aspect of the invention is the provision of a tool for implanting the anti-reflux valve prosthesis of this alternative embodiment wherein the annular body is internally threaded and the spikes are attached to a proximal end of the annular body. The tool includes an inner tube, a nipple secured to a distal end of the inner tube for releasably threadably coupling the annular body, and a handle secured adjacent to a proximal end of the inner tube for manipulation thereof. An overtube is slidable along and receives the inner tube. A handle is secured to a proximal end of the overtube for manipulation. A shield is attached to a distal end of the overtube. The shield is longitudinally movable between a first position for receiving the fixation spikes in the inwardly bent configuration during peroral insertion into the esophagus, a second position for releasing the fixation spikes, and a third position for facilitating return of the fixation spikes to the memory position.

Another aspect of the invention is a method of using the tool just described for implanting the anti-reflux valve prosthesis. The method comprises: (a) threadably engaging the nipple in the annular body; (b) bending the spikes inwardly and positioning the shield in the first position over the spikes; (c) perorally inserting the valve prosthesis into the esophagus near the gastroesophageal junction; (d) while holding the valve prosthesis in place, moving the shield into the second position to release the spikes to return to the memory position; (e) optionally moving the shield into the third position to facilitate return of the spikes into the memory position to facilitate engagement of the spikes in a wall of the esophagus; (f) rotating the inner tube with respect to the annular body to uncouple the nipple; and (g) withdrawing the tool from the esophagus.

A further aspect of the invention is a tool for extracting the anti-reflux valve prosthesis of the alternate embodiment wherein the annular body is internally threaded and the spikes are attached to a proximal end of the annular body. The tool includes inner and outer concentric tubes, a nipple secured to a distal end of the inner tube for threadably coupled the annular body, and a handle secured adjacent to a proximal end of the inner tube for manipulation thereof. The inner tube and the outer tube are in threaded interengagement for advancement of the outer tube by rotating the outer tube with respect to the inner tube. A crown is secured to a distal end of the outer tube and has a plurality of tangentially projecting shoes disposed on a distal end of respective longitudinal arms spaced along a circumference of the crown in correspondence with the spikes for bending the fixation spikes inwardly. An overtube has a shield of enlarged diameter at a distal end. The overtube is slidable over the outer tube to receive the plurality of inwardly bent spikes within the shield to inhibit laceration of the esophagus during movement of the prosthesis.

A still further aspect of the invention is a method of using the tool just described for extracting the anti-reflux valve prosthesis. The method includes: (a) perorally inserting the tool into the esophagus and threadably engaging the nipple in the annular body of the prosthesis; (b) while holding the inner tube in place, rotating the outer tube with respect to the inner tube to advance the crown with respect to the nipple, engage the spikes with the shoes and bend the fixation spikes radially inwardly; (c) advancing the overtube to position the shield over the inwardly bent spikes; and (d) withdrawing the tool and the prosthesis from the esophagus.

DETAILED DESCRIPTION

As exemplified by the figures wherein like numerals refer to like parts, the present invention provides a peroral prosthesis system for treatment of gastroesophageal reflux disease (GERD) in a patient comprising an anti-reflux valve prosthesis, a peroral implantation tool for perorally inserting and positioning the valve prosthesis at the distal end of the lumen of the esophagus and implanting or fixing the valve prosthesis to the lumen wall, and a peroral extraction tool for removing the prosthesis.

Figure 1:
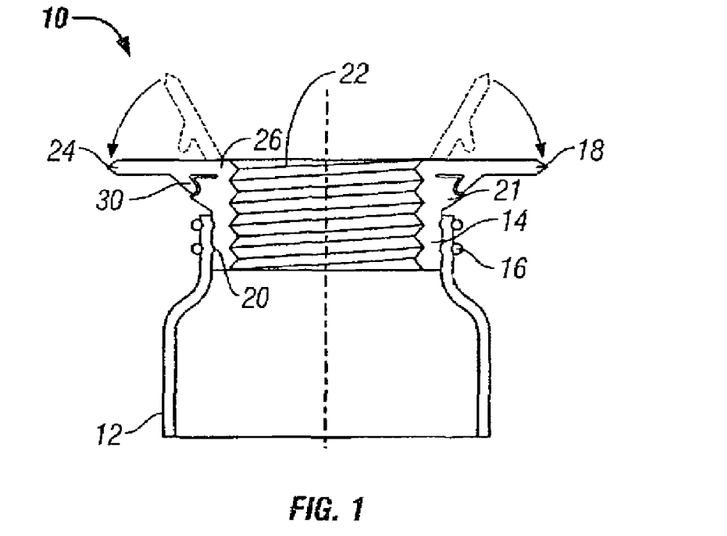
FIG. 1 is a side sectional view of a preferred embodiment of the antivalve prosthesis according to the present invention.
Figure 2:
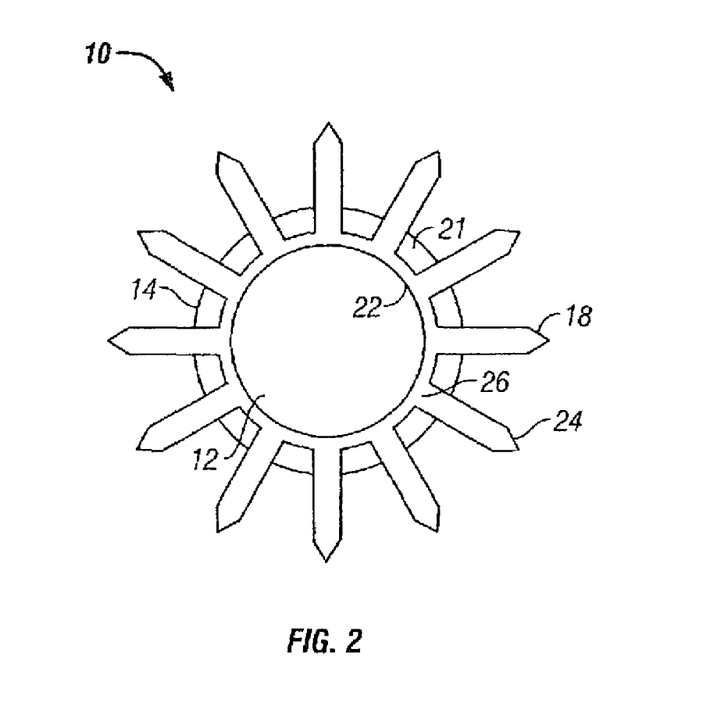
FIG. 2 is a top plan view of the prosthesis of FIG. 1 showing the fixation spikes in a deployed configuration.

Referring to FIGS. 1–2, in a preferred embodiment, the present invention provides a valve prosthesis 10 comprising a valve 12, preferably of the sleeve type, depending from an annular body 14. The sleeve valve 12 is made of a tubular membrane such as a tube of silicone, latex, polyester, or preferably GORE-TEX or TEADIT fluoropolymer, and has an upper end having a circular cross-section for mounting to the annular body 14 via rings 16, which can be made of a suitably inert material such as stainless steel or heat-shrink TEFLON tubing. The lower end of the sleeve valve 12 is preferably flat to facilitate closure upon exertion of pressure from the gastric contents, thereby preventing reflux or retrograde passage of gastric contents through the valve 12 under normal conditions. In a preferred embodiment, the sleeve is a semipermeable membrane that is essentially impervious to liquid but allows gas permeation to facilitate relief and ease discomfort from gas bloat, e.g. GORE-TEX film. If desired, the sleeve valve 10 can be designed to evert when excessive gastric pressures are present, as in regurgitation.

The annular body 14 is made from a biologically inert material such as TEFLON, fluorinated ethylene-propylene copolymer (FEP) or polytetrafluoroethylene (PTFE), or the like, and serves as a mounting ring for the sleeve valve 12, carrying an array of fixation spikes 18, preferably at an upper or proximal end thereof. The main portion of the body 14 can have a pair of grooves 20 formed in the exterior surface near the distal or lower end to facilitate retention of the rings 16 and form a seal between the valve 12 and the body 14. A shoulder 21 is formed in the exterior surface near the proximal end of the main body to serve as a keeper to lock the spikes 18 in position for fixation, as discussed in more detail below.

The main portion of the annular body 14 can be internally threaded, for example, with special acme right hand threads 22 that are relatively large with a high pitch and rounded or contoured bottoms to facilitate threaded engagement for implantation and extraction, and also to inhibit the retention and accumulation of swallowed material as it passes through. For example, the threads 22 are formed in one preferred embodiment with the dimensions given for medium size threads (7 threads per inch) for rolled threads for screw shells of electric sockets and lamp bases, American Standard, in the *Machinist's Handbook*. The inside diameter of the annular body 14 should be large enough so as to facilitate the orthograde passage of food and liquids through the esophagus, e.g. about 25 mm. The outside diameter of the annular body 14, especially at the shoulder 21, should be sufficiently large to seat firmly in the esophagus with some slight stretching of the lumen wall to facilitate the formation of a fluid-tight seal therewith.

Figure 3:
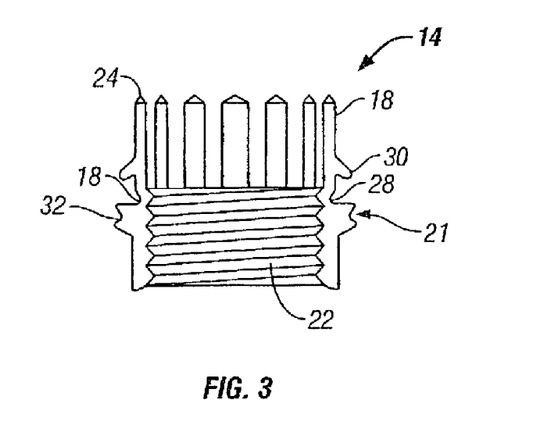
FIG. 3 is a side sectional view of the annular body used in the prosthesis of FIG. 2 showing the fixation spikes in a longitudinal, pre-deployment configuration.
Figure 4:
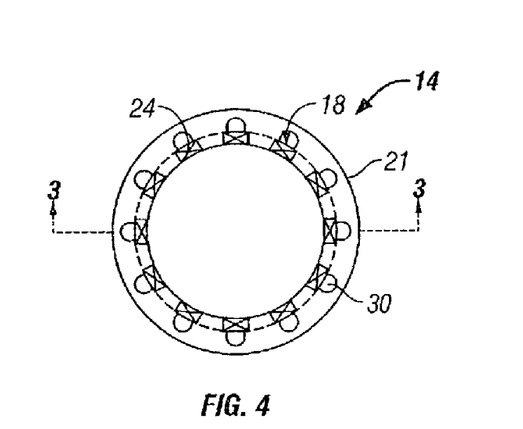
FIG. 4 is a top view of the annular body of FIG. 3.
Figure 5:
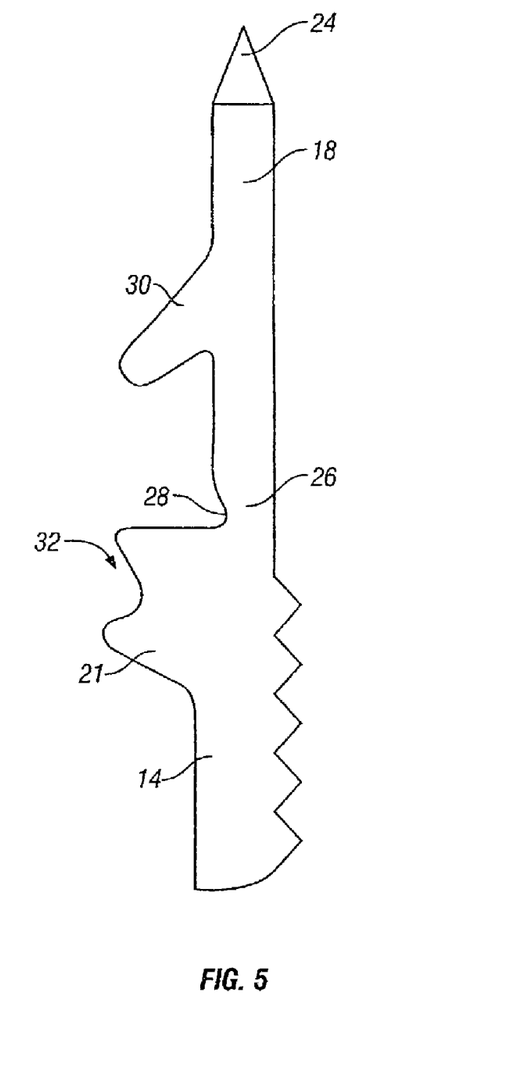
FIG. 5 is an enlarged sectional view of the upper end of the annular body showing a preferred embodiment of the outer edge profile.

The spikes 18 are evenly spaced along the circumference of the annular body 14 as best seen in FIGS. 2–4. Each spike 18 has a pointed or sharpened tip 24 and a flexible or hinged base 26 secured to the main portion of the annular body 14. The spikes 18 are preferably integrally formed with the main portion of the body 14, but can have a smaller thickness than the wall of the main body. For example, $\frac{1}{16}$" thick spikes may be utilized with a main body thickness of $\frac{3}{32}$". To facilitate bending of the spikes 18, a notch 28 can be provided at the base 26, preferably leaving sufficient thickness so that the spike 18 is biased upwardly to facilitate the extraction process. A downwardly sloped arm 30 disposed between the tip 24 and base 26 extends radially outwardly from each fixation spike 18 and functions as a dog to lock the spike 18 into place for fixation in the lumen wall. The arm 30 and the shoulder 21 are complementarily dimensioned and positioned so that a lower surface of the arm 30 is securely retained against inwardly tapered shelf 32 formed in the shoulder 21. The proximal surface of the shoulder 21 is preferably at a right angle to an axis of the body 14 to help position the spikes 18 at a corresponding right angle. The distal surface of the shoulder 21 can be sloped to generally correspond approximately to the angle of the arm 30.

Figure 6:
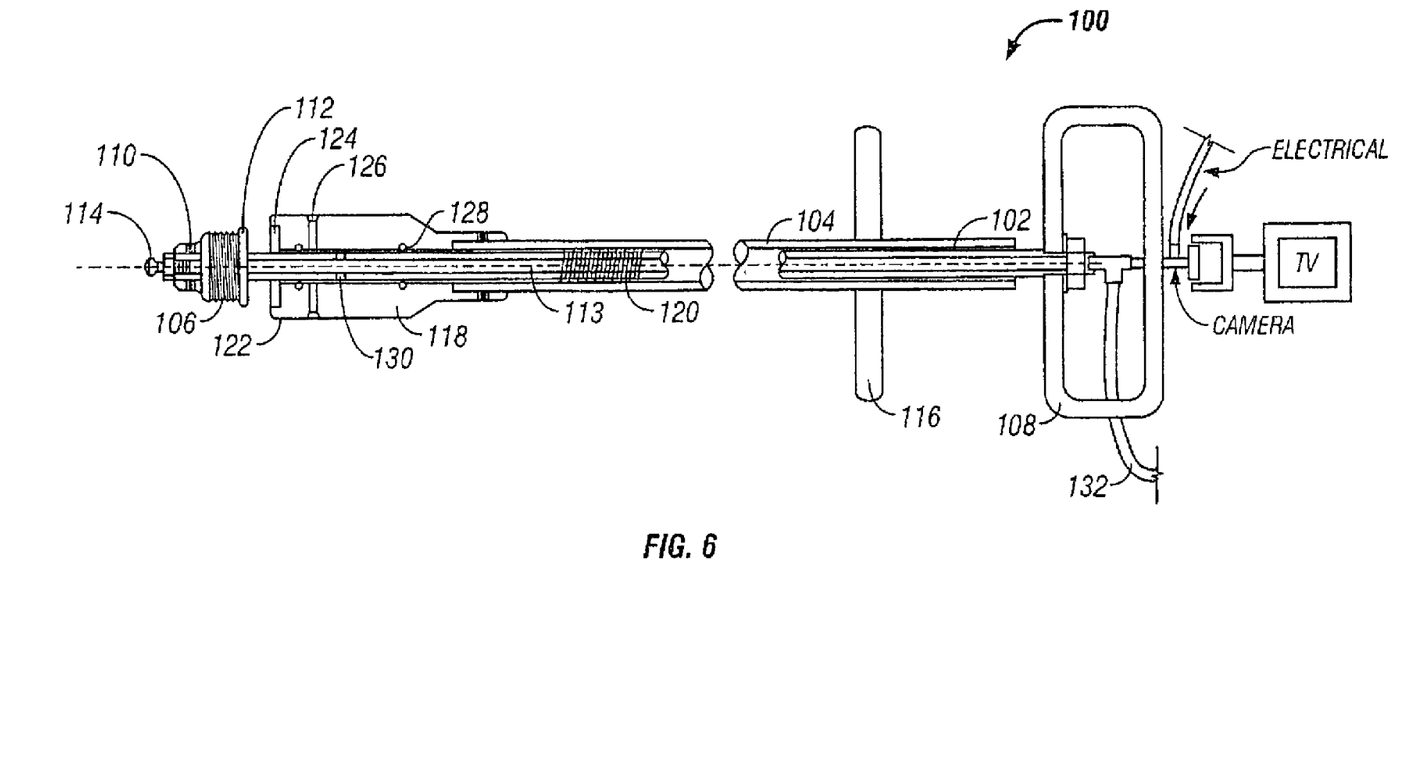
FIG. 6 is a side view, partly in section and partly cut away, of an insertion tool according to the present invention for peroral implantation of the anti-reflux valve prosthesis of FIGS. 1–5.
Figure 9:
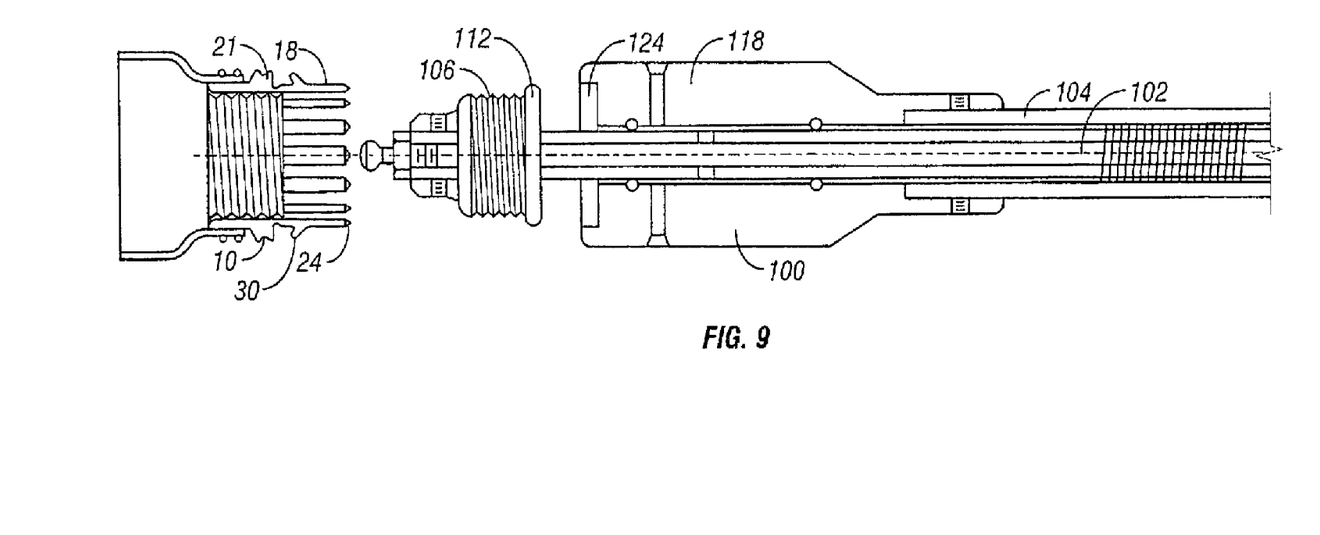
FIG. 9 is an exploded side view, partly in section and partly cut away, of an insertion tool-prosthesis assembly in preparation for implantation of the anti-reflux valve prosthesis of FIGS. 1–5 with the tool of FIG. 6.

With reference to FIG. 6, there is illustrated a tool 100 that can be used to insert or implant the prosthesis 10. The tool 100 has an inner tube 102 received within an outer tube 104. The tubes 102 and 104 can be rigid or flexible, as desired, preferably made of autoclavable and/or sterilizable materials or combinations of materials such as stainless steel, polypropylene or the like. The inner tube 102 is provided with a nipple 106 at the distal end and a manipulating handle 108 at the proximal end. The nipple 106 is threaded on an exterior surface to threadably engage the prosthesis 10 (See FIG. 9) in preparation for peroral insertion. The nipple 106 preferably has an elongated distal end 110 of reduced outside diameter to facilitate engagement with the prosthesis 10, and a proximal end 112 of slightly enlarged outside diameter to slightly bias the fixation spikes 18 outwardly upon engagement of the prosthesis 10. If desired, the inner tube 102 is provided with a central passage 113 for equipping an optics package 114 including a light source and a fiber optic cable and/or a conventional endoscope.

The outer tube 104 is provided with a proximal handle 116 and a distal headpiece 118. The outer tube is threadedly connected to the inner tube 102 at threaded section 120, which preferably has left-handed or opposite-direction standard threads. The headpiece 118 has a relatively enlarged outside diameter 122 so as to bend the fixation spikes 18 outwardly as the outer tube is advanced along the inner tube 102 by counterclockwise rotation of the outer tube 104 while the inner tube 102 is held stationary. The left-handed threads ensure that the rotation of the outer tube 104 does not tend to turn the prosthesis 10. The headpiece can have a recess 124 formed in a distal end surface to shoulder the proximal end 112 and ensure that the fixation spikes are fully deployed and locked in place.

If desired, the tool 100 can be provided with a passageway to apply vacuum adjacent the prosthesis to draw the lumen wall inwardly and facilitate penetration of the spikes 18. The headpiece 118 is provided with a plurality of transverse passages 126 in communication with an annulus defined by the inside diameter of the headpiece 118, the outside diameter of the inner tube 102, and opposing O-ring seals 128 on either side thereof. A transverse bore 130 is formed in the inner tube 102 in fluid communication between the annulus and the central passageway 113. A vacuum hose 132 connects the proximal end of the central passageway 113 to a conventional vacuum source.

Figure 7:
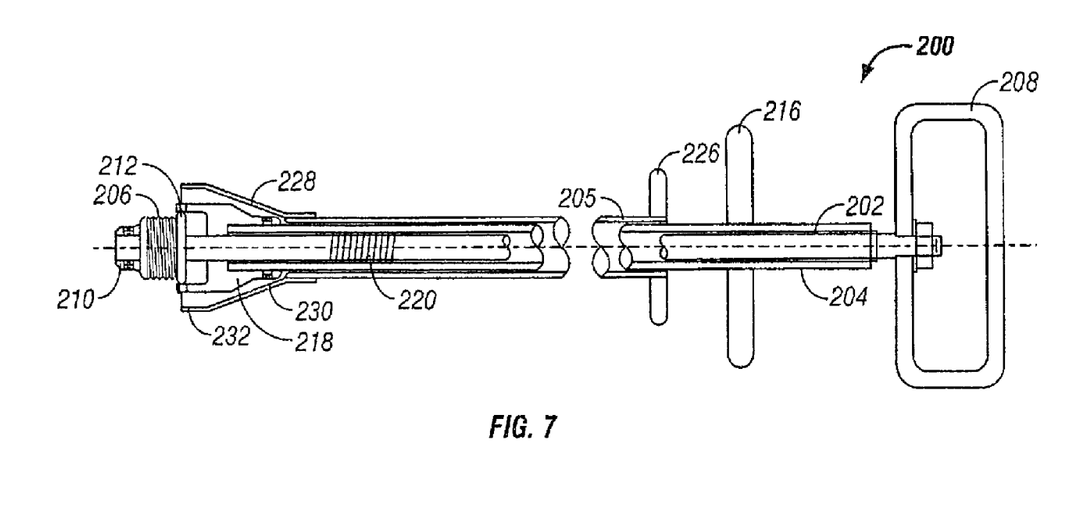
FIG. 7 is a side view, partly in section and partly cut away, of an extraction tool according to the present invention for peroral removal of the anti-reflux valve prosthesis of FIGS. 1–5.

With reference to FIG. 7, there is illustrated a tool 200 that can be used to remove or extract the prosthesis 10. This can be desirable if the prosthesis 10 is not functioning properly for the patient, e.g. if the lumen stretches and fails to seal against the prosthesis 10, the valve 12 leaks, the prosthesis 10 irritates the patient, or the like. The tool 200 has an inner tube 202 received within an outer tube 204, which in turn can be received within an overtube 205. The tubes 202, 204 and 205 can be rigid or flexible, as desired, preferably made of autoclavable and/or sterilizable materials or combinations of materials such as stainless steel, polypropylene or the like. The inner tube 202 is provided with a nipple 206 at the distal end and a manipulating handle 208 at the proximal end. The nipple 206 is threaded on an exterior surface to threadably engage the prosthesis 10 in preparation for extraction. The nipple 206 preferably has an elongated guide member 210 of reduced outside diameter at a distal end to facilitate engagement with the prosthesis 10, and a proximal end 212 of slightly enlarged outside diameter for shouldering upon threaded engagement of the prosthesis 10. If desired, the inner tube 202 can be provided with a central passage for equipping an optics package including a light source and a fiber optic cable and/or a conventional endoscope, as in the insertion tool 100 (see FIG. 6).

Figure 8:
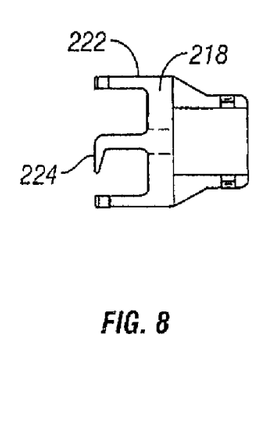
FIG. 8 is a simplified schematic of the crown of the extraction tool of FIG. 7 showing the extraction foot detail.

The outer tube 204 is provided with a proximal handle 216 and a distal crown 218. The outer tube 204 is threadedly connected to the inner tube 202 at threaded section 220, which preferably has left-handed or opposite-direction standard threads. As best seen in FIG. 8, the crown 218 has a plurality of evenly spaced longitudinal arms 222, each carrying a tangential extraction shoe 224 along a circle in the proximal surface of the shoulder 21 of the prosthesis 10, in one-to-one correspondence between the spikes 18 and the shoes 224. The shoes 224 are designed with a thickness increasing from a forward point to the respective arm 222, such that, upon advancement of the outer tube 204 by counterclockwise rotation, they catch between a respective spike 18 and the shoulder 21, and upon further counterclockwise rotation, they force the spikes 18 upwardly and disengage the arms 30 from the shelves 32, unlocking the spikes 18.

The overtube 205 is slideabe over the outer tube 204, and is provided with a proximal handle 226 and a distal shield 228. The shield 228 has a frustoconical section 230 flared outwardly from a small diameter adjacent the overtube 205 to a maximum diameter adjacent to a relatively short cylindrical section 232 at a free distal end thereof. The diameter of the cylindrical section 232 is larger than the diameter of the crown 218, but less than the diameter of the deployed spikes 18 to house the spikes 18 during retraction of the prosthesis 10 from the esophagus.

Figure 10:
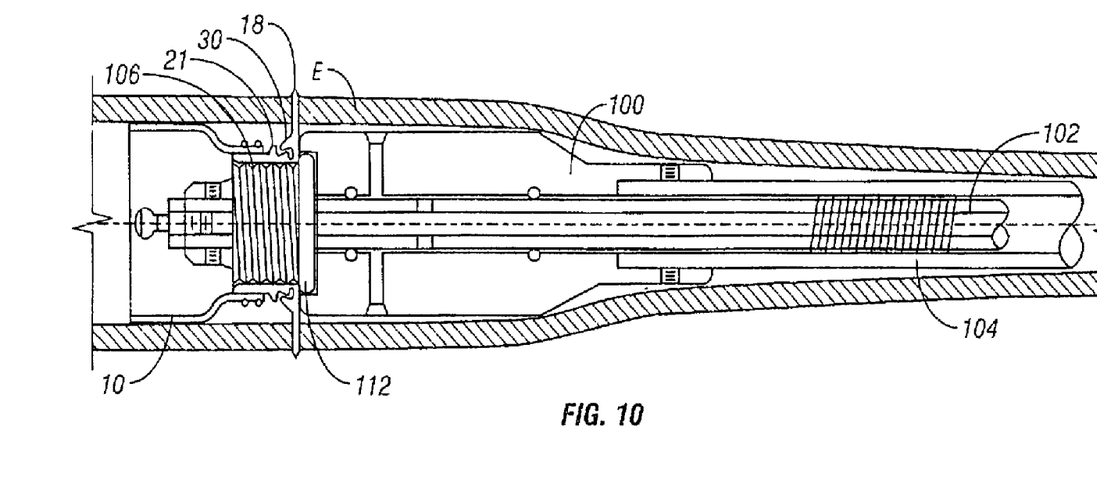
FIG. 10 is a side view, partly in section and partly cut away, of the distal end of the insertion tool-prosthesis assembly of FIG. 9 showing implantation of the prosthesis in the esophageal lumen following deployment of the fixation spikes and application of the vacuum source prior to disengagement of the tool from the prosthesis.

To use the insertion tool 100 to implant the prosthesis 10, the prosthesis 10 is threaded onto the nipple 106 of the insertion tool 100 as shown in FIG. 10, shouldering the prosthesis 10 against the enlarged diameter 112 and pushing the spikes 18 slightly outwardly. The outer tube 104 at this time is in a retracted position, with the headpiece 118 spaced from the spikes 18. If desired, the headpiece 118 (see FIG. 20) can be advanced along the inner tube 102 until the distal end just touches the tips 24 (see FIG. 9) of the spikes 18 to ensure that further advancement of the headpiece 118 will push the spikes outwardly. Then the assembly is inserted through the mouth and into the esophagus E to position the prosthesis 10 at the desired location of implantation, e.g. at the gastroesophageal junction.

Holding the inner tube 102 and the prosthesis 10 in place, the headpiece 118 is advanced by rotating the outer tube 104 counterclockwise to push the spikes 18 outwardly until the enlarged diameter 112 shoulders into the recess 124 and the arms 30 are locked into place in cooperation with the shoulders 21. If desired, the vacuum source can be connected and actuated for a brief period to draw in the lumen of the esophagus and facilitate penetration of the spikes 18, which preferably perforate the esophagus E. The inner tube 102 is then rotated counterclockwise to release the threaded engagement with the prosthesis 10 and the tool 100 is retracted, leaving the prosthesis 10 in place.

Figure 11:
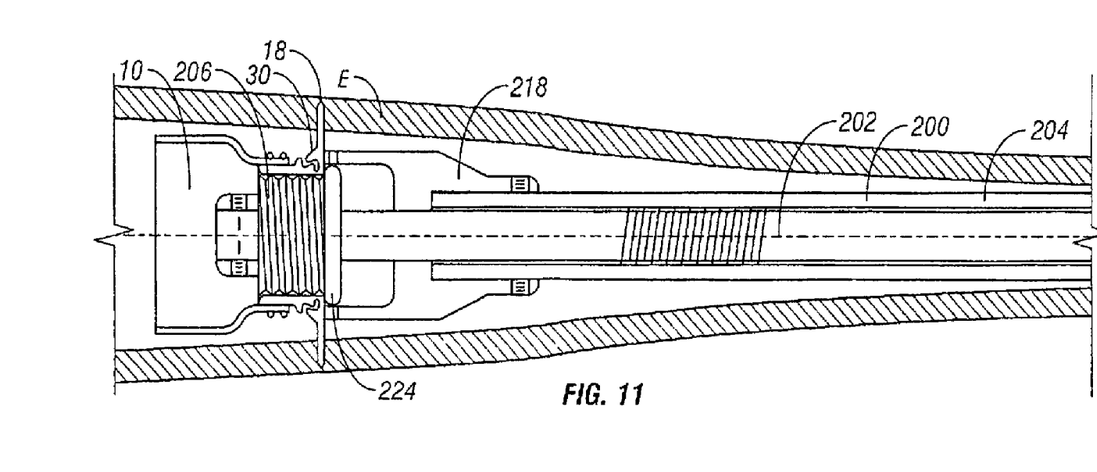
FIG. 11 is a side view, partly in section and partly cut away, of the distal end of the extraction tool of FIGS. 7–8 threaded into the prosthesis of FIGS. 1–5 implanted in a patient's esophagus in preparation for foot release extraction according to one embodiment of the present invention.
Figure 12:
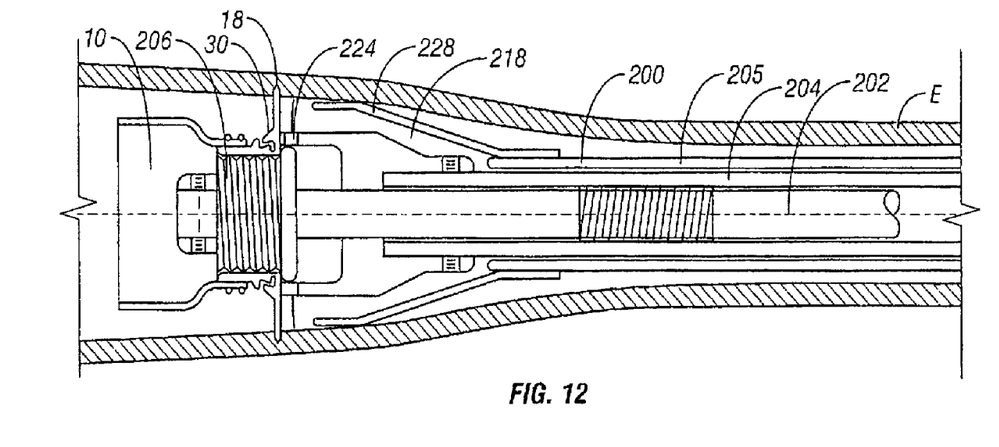
FIG. 12 is a side view, partly in section and partly cut away, of the distal end of the extraction tool-prosthesis assembly of FIG. 11 in a patient's esophagus with the overtube shield positioned in preparation for foot release extraction according to one embodiment of the present invention.
Figure 13:
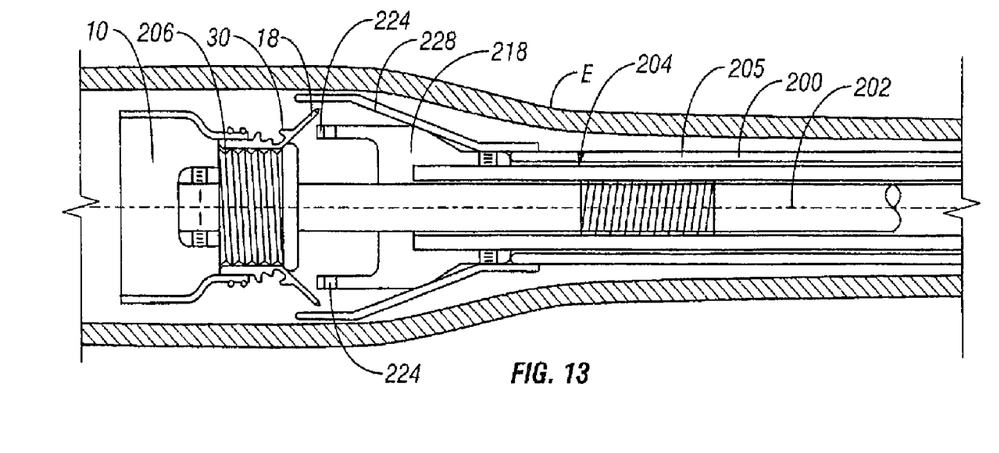
FIG. 13 is a side view, partly in section and partly cut away, of the distal end of the extraction tool-prosthesis assembly of FIG. 12 with the overtube shield advanced in position over the fixation spikes following the foot release extraction step and the assembly being removed from the patient's esophagus according to one embodiment of the present invention.

As seen in FIG. 11, to remove the prosthesis 10 previously implanted in the esophagus, the distal end of the tool 200 is inserted through the mouth and down the esophagus E until it contacts the prosthesis 10. The nipple 206 is threaded into the prosthesis 10 by rotating the inner tube 202 clockwise with the handle 208, and then by turning the outer tube 204 counterclockwise, the crown 218 is shouldered up against the spikes 18. The overtube 205 can then be advanced to position the shield 228 near the spikes 18, as shown in FIG. 12. This stretches the esophageal lumen outwardly to help retract the spikes 18. Further rotation of the outer tube 204 engages the extraction feet 224 between the base of the spikes 18 and the proximal surface of the shoulder 30, and dislodges the arms 30 to unlock the spikes 18. The spikes 18 are biased or have some memory to return inwardly toward a longitudinal orientation, but if desired, the tool 200 can be advanced in the esophagus E to facilitate release of the spikes 18. The overtube shield 228 is then advanced over the prosthesis 10 to hold the spikes 18 and minimize interference or catching on the lumen wall, as illustrated in FIG. 13. The tool 200 is then retracted, removing the prosthesis 10 from the esophagus.

Figure 14:
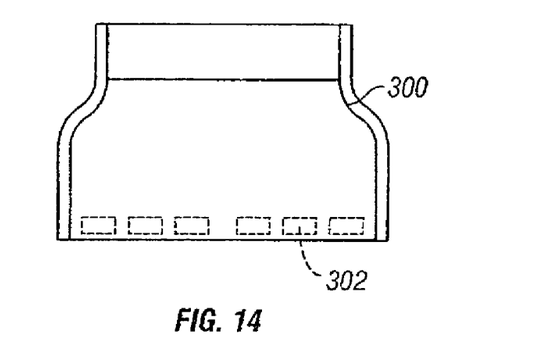
FIG. 14 is a side view of an alternate embodiment of an antisleeve valve having embedded magnets for use with the annular body of FIGS. 3–5.
Figure 15:
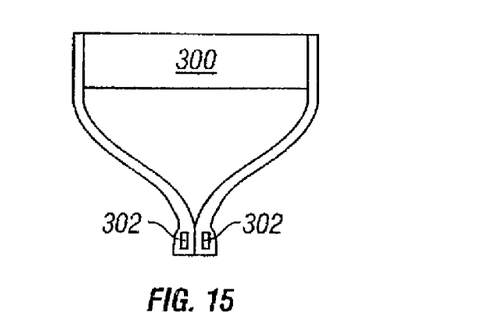
FIG. 15 is an end sectional view of the valve of FIG. 14.
Figure 16:
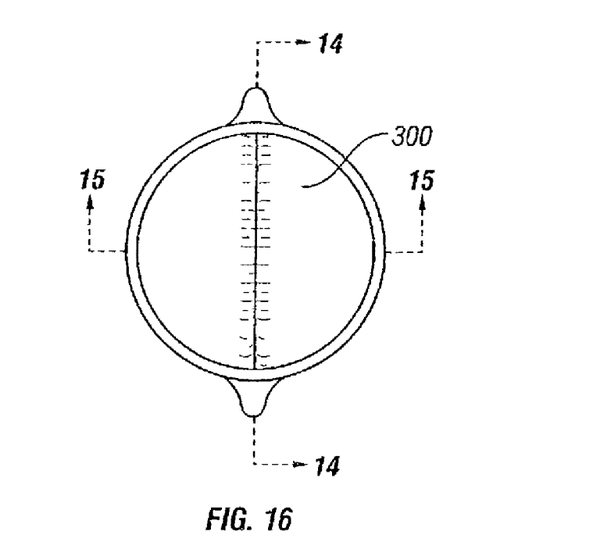
FIG. 16 is a top view of the valve of FIGS. 14–15.
Figure 17A:
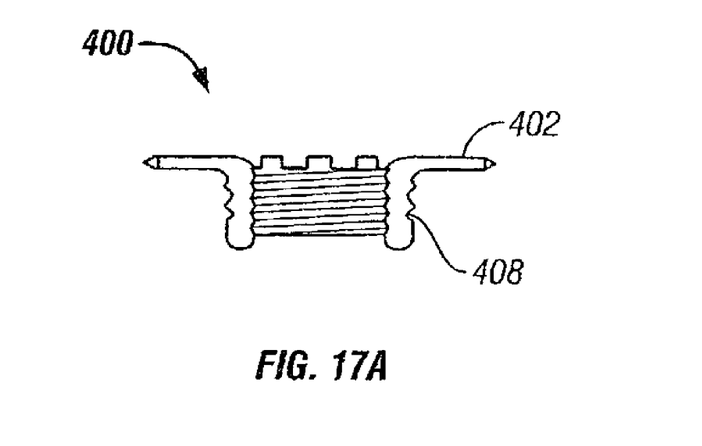
FIGS. 17A and 17B are side sectional and top plan views, respectively, of an alternate embodiment of the annular body used in the anti-reflux valve prosthesis of the invention wherein the spikes are secured in a deployed configuration for implantation in the lumen of the esophagus.
Figure 17B:
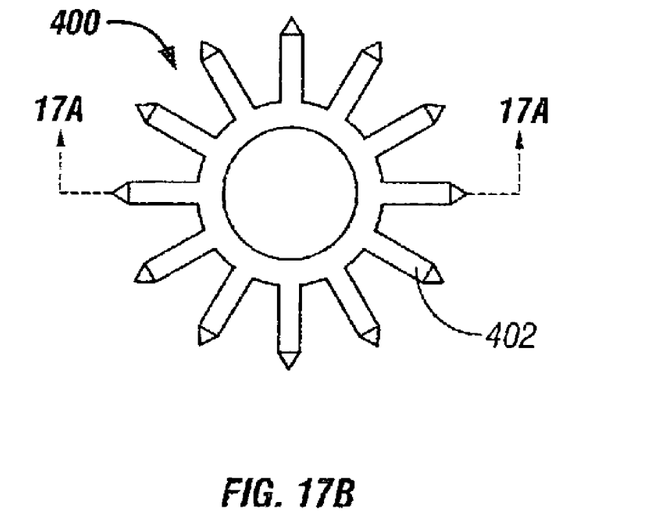

FIGS. 14–16 illustrate an alternate embodiment of a sleeve valve 300 that uses magnets 302 embedded within the tubing material near the distal end thereof. The valve 300 is in all respects otherwise similar to the valve 12 illustrated in the prosthesis 10 of FIG. 1. The magnets 302 are paired with opposite poles in an opposing magnet 302" in the opposing side of the valve 300 to facilitate closure, yet the magnetic force is not so strong as to inhibit opening of the valve for orthograde passage of food and liquids. The magnets 302 also serve to facilitate detection by x-ray or other radiographic imaging techniques.

FIGS. 17A, 17B, and 18–21 illustrate an alternate embodiment wherein the annular body 400 is formed with fixation spikes 402 that are in an outwardly radiating configuration with memory for positioning the spikes 402 in a deployed configuration, ready for implantation in the lumen of the esophagus. The annular body 400 can be formed, for example, by injection molding or transfer molding the fluorinated polymer in the shape of a blank having a tubular section and a disk portion that extends radially outwardly from one end of the tubular section. The fixation spikes 402, internal threads 404 and external sleeve valve 406 (see FIGS. 18–20) retention grooves 408, are then formed by milling or machining the blank. The fixation spikes 402 have some flexibility so that they can be bent slightly to facilitate insertion and removal, but also have memory to return to the outwardly radiating configuration to facilitate implantation once the prosthesis is properly positioned in the esophagus for implantation. It is not necessary for the fixation spikes 402 to have immediate memory, and can, if necessary, take several minutes to return to the memory position (radial deployment), or if desired, can be assisted into the memory position by mechanical and/or slight heating to body temperature.

Figure 18:
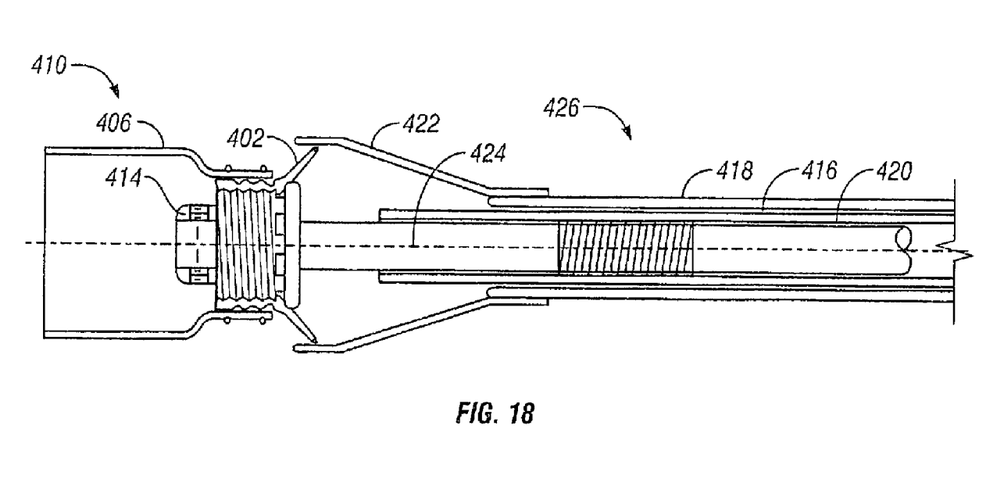
FIG. 18 is a side view, partly in section and partly cut away, of an assembly of a valve prosthesis made with the annular body of FIGS. 17A and 17B coupled to the distal end of an insertion tool in preparation for peroral insertion.

As best seen in FIG. 18, to implant the prosthesis 410, it is threaded onto the nipple 414 on the distal end of implantation tool 416, which is generally similar to the implantation tool 100 of FIG. 6. The implantation tool 416 has an overtube 418, which is longitudinally slideable over an outer tube 420. A shield 422 of enlarged diameter is secured to the distal end of the overtube 418. To prepare the assembly for peroral implantation, the fixation spikes 402 are bent upwardly toward the proximal end, and the overtube 418 and shield 422 are moved forwardly so that the spikes 402 are received within the shield 422. The distal end of the assembly is then inserted perorally to position the prosthesis 410 near the esophageal junction or other location at which it is desired to be fixed, while retaining the spikes 402 within the shield 422 so as to avoid laceration by the spikes 402.

Figure 19:
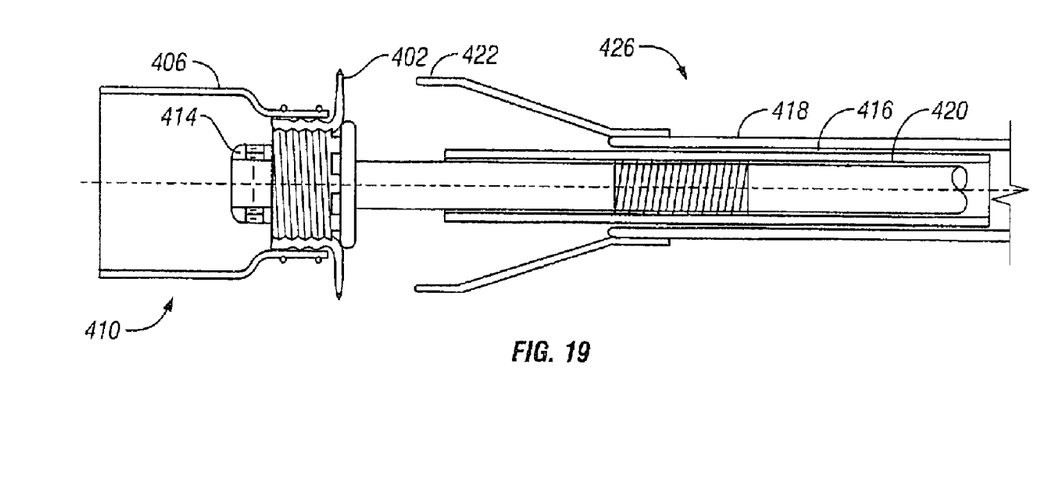
FIG. 19 is a side view, partly in section and partly cut away, of the assembly of FIG. 18 following peroral placement of the prosthesis near the gastroesophageal junction and retraction of the overtube to deploy the fixation spikes.

Once placed in the desired location within the esophagus, the overtube 418 and shield 422 are retracted to release the spikes 402 (See FIG. 19). The spikes 402 have memory to return to the outwardly disposed configuration and pierce the lumen wall to fix the prosthesis 410 in place. If desired, the spikes 402 can be mechanically assisted by a sliding the shield 422 forward and pushing against the proximal surfaces of the spikes 402. The tool 416 can also include modifications for applying a vacuum to the esophagus to facilitate impaction of the fixation spikes 402 into the wall of the esophagus, as in the embodiment of FIGS. 9–10, or rapidly retracting the shield 422 to the position shown in FIG. 19 can also induce an impaction-facilitating localized vacuum. In addition, slightly retracting the prosthesis 410 with the implantation tool 416 after the tips of the fixation spikes have caught on the lumen wall can also serve to facilitate impaction. The implantation tool 416 is then disconnected by rotating the inner tube 424 to unthread the nipple 414 from the prosthesis 410, and withdrawn from the esophagus to leave the prosthesis 410 fixed in place to inhibit reflux.

Figure 20:
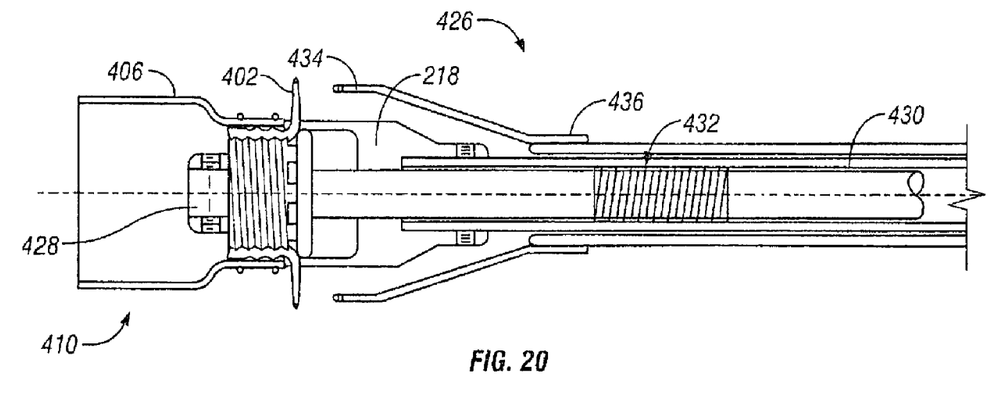
FIG. 20 is a side view, partly in section and partly cut away, of an assembly of the valve prosthesis in FIGS. 17–19 coupled to the distal end of a peroral extraction tool in preparation for removal.
Figure 21:
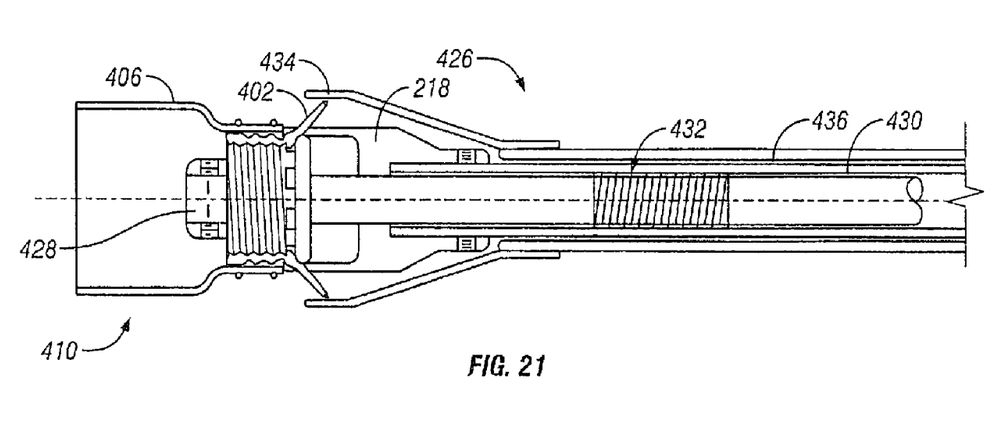
FIG. 21 is a side view, partly in section and partly cut away, of an assembly of FIG. 20 following retraction of the fixation spikes within the overtube shield in preparation for peroral removal from the esophagus.

In the event that it is desired to remove the prosthesis 410, the extraction tool 426 of FIGS. 20–21, which is generally similar to the extraction tool 200 of FIGS. 7–8, is inserted perorally and the nipple 428 on the distal end thereof is threaded into the annular body 400 until it shoulders as shown in FIG. 20. The outer tube 430 is then advanced by means of opposite-direction threads 432 so that the extraction shoes 224 on the distal end of the crown 218 (see FIG. 8) engage below the fixation spikes 402, and continued rotation of the outer tube 430 bends the spikes 402 upwardly or toward the proximal end of the tool 426 until they can be received within the shield 434 carried on the distal end of the overtube 436, which is slideable over the outer tube 430 into position as shown in FIG. 21. Removal of the spikes 402 is facilitated by the localized expansion of the lumen by the shield 434, and also by advancing the prosthesis 410 slightly with the tool 426. Additionally, air or another inert gas can be injected into the esophagus, or a balloon (not shown) could be inflated around or just below the prosthesis 410.

While the above description contains many specifics, these should not be construed as limitations on the scope of the invention, but rather as exemplifications of preferred embodiments thereof. Many other variations are possible, which would be obvious to one skilled in the art. Accordingly, the scope of the invention should be determined by the scope of the appended claims and their equivalents, and not just the illustrative embodiments.

We claim:

1. An anti-reflux valve prosthesis to be placed in an esophagus, the prosthesis comprising:
    an annular fixation body;
    a plurality of retractable spikes spaced along a circumference of the annular body adjacent one end thereof to secure the prosthesis in the esophagus;
    a one-way valve depending from the annular fixation body, the one way valve configured to allow orthograde passage therethrough and to inhibit retrograde passage of gastric contents; and
    a gas permeable membrane to allow retrograde permeation of a gas therethrough.

2. The anti-reflux valve prosthesis of claim 1 wherein the prosthesis is configured to be perorally installed.

3. The anti-reflux valve prosthesis of claim 2 wherein the prosthesis is configured to be perorally removable.

4. The anti-reflux valve prosthesis of claim 1 wherein the gas permeable membrane is substantially liquid impermeable.

5. The anti-reflux valve prosthesis of claim 1 wherein the one-way valve is a sleeve valve.

6. The anti-reflux valve prosthesis of claim 1 wherein the prosthesis is comprised of a biologically inert material.

7. The anti-reflux valve prosthesis of claim 6 wherein the prosthesis is comprised of a fluorinated polymer.

8. An anti-reflux valve prosthesis for peroral implantation in an esophagus, the prosthesis comprising:
   an annular body;
   a valve depending from the annular body, said valve allowing orthograde passage therethrough and inhibiting retrograde passage of gastric contents; and
   a plurality of spikes spaced along a circumference of the annular body adjacent one end thereof, wherein each of the spikes includes a tip at a free end thereof and a base attached to the annular body and are selectively retractable between a deployed and a retracted alignment with respect to the circumference, and
   a dog formed between a base and a tip of each of the spikes.

9. The anti-reflux valve prosthesis of claim 8 wherein said valve is a sleeve valve.

10. The anti-reflux valve prosthesis of claim 9 wherein said sleeve valve comprises a plurality of magnets, the magnets secured at a distal end thereof to facilitate closure of the sleeve valve.

11. The anti-reflux valve prosthesis of claim 8 further comprising a gas permeable membrane to allow retrograde permeation of gas therethrough.

12. The anti-reflux valve prosthesis of claim 11 wherein the gas permeable membrane is substantially liquid impermeable.

13. The anti-reflux valve prosthesis of claim 8 wherein a plurality of keepers are positioned on an exterior surface of the annular body for receiving the dogs and locking the spikes in the deployed alignment.

14. The anti-reflux valve prosthesis of claim 8 wherein each of the spikes is outwardly bendable at the base between the retracted alignment and the deployed alignment.

15. The anti-reflux valve prosthesis of claim 14 wherein said retracted alignment is generally longitudinal.

16. The anti-reflux valve prosthesis of claim 14 wherein said deployed alignment is generally radially outward.

17. The anti-reflux valve prosthesis of claim 8 further comprising a tool to perorally insert the prosthesis into the esophagus.

18. The anti-reflux valve prosthesis of claim 8 further comprising a tool to perorally remove the prosthesis from the esophagus.

19. The anti-reflux valve prosthesis of claim 9 wherein the annular body is internally threaded.

20. The anti-reflux valve prosthesis of claim 8 wherein the valve is implanted to relieve symptoms of a patient with Gastroesophageal reflux disease.

21. The anti-reflux valve prosthesis of claim 20 wherein the patient does not suffer from esophageal cancer.

22. An implantation tool in combination with the anti-reflux valve prosthesis of claim 8, the tool comprising:
   an inner tube and an outer tube, said tubes being generally concentrically aligned;
   a nipple secured to a distal end of the inner tube, the nipple coupled with the annular body of the anti-reflux valve prosthesis; and
   a headpiece secured to a distal end of the outer tube to engage the retractable spikes and outwardly extend them into position by advancing the headpiece into abutment with the nipple.

23. The combination of claim 22 wherein the outer tube is configured to be advanced or retracted as the outer tube is rotated with respect to the inner tube.

24. The combination of claim 23 further comprising a handle, said handle being secured adjacent to a proximal end of the inner tube for manipulation thereof.

25. The combination of claim 24 further comprising a second handle secured adjacent to a proximal end of the outer tube to facilitate rotation of the outer tube with respect to the inner tube.

26. The combination of claim 22 further comprising a fiber optic cable disposed within a central longitudinal passage of the inner tube for viewing the esophagus.

27. The combination of claim 22 wherein the headpiece includes a plurality of transverse passages formed therein in communication with a transverse bore in a wall of the inner tube and a central longitudinal passage.

28. The combination of claim 27 further including a vacuum source in communication with the central longitudinal passage.

29. An implantation tool in combination with the anti-reflux prosthesis of claim 8, the tool comprising:
   the anti-reflux valve prosthesis of claim 8;
   means for mounting the anti-reflux valve prosthesis onto a headpiece of the tool;
   means for positioning the anti-reflux valve prosthesis in the esophagus;
   means for deploying the plurality of radial spikes with the tool;
   means for pulling a vacuum across a longitudinal passage of the tool; and
   means for drawing a lumen of the esophagus inwardly for facilitating impaction of the spikes.

30. An implantation tool in combination with the anti-reflux valve prosthesis of claim 8, the tool comprising:
   means for perorally inserting and positioning the anti-reflux valve prosthesis into the esophagus;
   means for deploying the plurality of spikes, the spikes depending radially from the anti-reflux prosthesis; and
   means for impaling the esophagus upon the spikes to hold the prosthesis in place.

31. An implant tool in combination with the anti-reflux prosthesis of claim 8 in an esophagus, the tool comprising:
   the anti-reflux valve prosthesis of claim 8;
   means for releasably engaging a nipple of the tool with the annular body of the prosthesis;
   means for perorally inserting the valve prosthesis in to the esophagus near a gastroesophageal junction;
   means for extending the spikes fully outward into a deployed alignment for engagement with a lumen of the esophagus;
   means for uncoupling the nipple from the prosthesis; and
   means for withdrawing the tool from the esophagus.

32. An extraction tool in combination with the anti-reflux valve prosthesis of claim 8, wherein the prosthesis includes radial spikes extended therefrom, the tool comprising:
   an inner tube and an outer tube, said tubes being generally concentrically aligned;

a nipple secured to a distal end of the inner tube, the nipple configured to be releasably coupled with the annular body; and a crown secured to a distal end of the outer tube, the crown having a plurality of tangentially projecting shoes to receive and retract the extended radial spikes.

33. The combination of claim 32 wherein the outer tube is configured to be advanced or retracted as the outer tube is rotated with respect to the inner tube.

34. The combination of claim 33 the tool further comprising a handle, the handle being secured adjacent to a proximal end of the inner tube for manipulation thereof.

35. The combination of claim 34 the tool further comprising a second handle secured adjacent to a proximal end of the outer tube to facilitate movement of the outer tube with respect to the inner tube.

36. The combination of claim 32 the tool further comprising a fiber optic cable disposed within a central longitudinal passage of the inner tube for viewing the esophagus.

37. The combination of claim 32 the tool further comprising an overtube having a shield of enlarged diameter at a distal end thereof, wherein the overtube is slidable over the outer tube to receive the plurality of spikes to facilitate removal of the prosthesis from the esophagus.

38. The combination of claim 37 wherein the shield is tapered from a larger diameter at a distal end to a smaller diameter at a proximal end.

39. The combination of claim 32 wherein the crown is configured to be removable and replaced with a headpiece, the headpiece configured to assist in reinstalling the prosthesis into the esophagus.

40. An extraction tool in combination with the anti-reflux prosthesis of claim 8, the tool comprising:

means for perorally inserting the tool into the esophagus, wherein the tool comprises a nipple and a crown;

means for engaging the nipple into the annular body of the prosthesis, wherein the plurality of spikes are extended;

means for advancing the crown with respect to the nipple, the crown configured to retract the spikes; and means for removing the tool and engaged prosthesis from the esophagus.

41. The anti-reflux valve prosthesis of claim 8, wherein the annular body includes a biologically inert polymer, further comprising:

a plurality of substantially rigid spikes spaced along a circumference of the annular body adjacent one end thereof extending radially outwardly from the annular body; and wherein each spike is temporarily inwardly bendable for implantation and has memory to return to the radially outwardly extending position.

42. An implantation tool in combination with the anti-reflux valve prosthesis of claim 41, wherein the annular body is internally threaded and the spikes are attached to a proximal end of the annular body, comprising:

an inner tube;

a nipple secured to a distal end of the inner tube for releasably threadably coupling the annular body;

a handle secured adjacent to a proximal end of the inner tube for manipulation thereof;

an overtube slideable along and receiving the inner tube;

a handle secured to a proximal end of the overtube for manipulation thereof;

a shield attached to a distal end of the overtube longitudinally movable between a first position for receiving the fixation spikes in the inwardly bent configuration during peroral insertion into the esophagus, a second position for releasing the fixation spikes, and a third position for facilitating return of the fixation spikes to the memory position.

43. An extraction tool in combination with the anti-reflux valve prosthesis of claim 41, wherein the annular body is internally threaded and the spikes are attached to a proximal end of the annular body, comprising:

inner and outer concentric tubes;

a nipple secured to a distal end of the inner tube for threadably coupling the annular body;

a handle secured adjacent to a proximal end of the inner tube for manipulation thereof;

wherein the inner tube and the outer tube are in threaded interengagement for advancement of the outer tube by rotating the outer tube with respect to the inner tube;

a crown secured to a distal end of the outer tube and having a plurality of tangentially projecting shoes disposed on a distal end of respective longitudinal arms spaced along a circumference of the crown in correspondence with the spikes for bending the fixation spikes inwardly;

an overtube having a shield of enlarged diameter at a distal end thereof, wherein the overtube is slidable over the outer tube to receive the plurality of inwardly bent spikes within the shield to inhibit laceration of the esophagus during movement of the prosthesis.

44. An implantation tool in combination with the anti-reflux prosthesis of claim 41, the tool comprising:

means for bending the plurality of spikes inwardly and means for positioning a shield in a first position over the spikes;

means for perorally inserting the prosthesis into the esophagus near a gastroesophageal junction;

means for moving the shield into a second position while holding the prosthesis in place to release the spikes into the memory position;

means for rotating an inner tube of the tool with respect to the annular body of the prosthesis to uncouple a nipple of the tool from the prosthesis; and means for withdrawing the tool from the esophagus.

45. An extraction tool in combination with the anti-reflux prosthesis of claim 41, the tool comprising:

means for perorally inserting the tool into the esophagus and threadably engaging a nipple of the tool in the annular body of the prosthesis;

means for rotating an outer tube of the tool with respect to an inner tube of the tool while holding the inner tube in place to advance a crown of the tool with respect to the nipple, to engage a plurality of spikes of the prosthesis with a plurality of shoes of the crown, and to bend the spikes radially inwardly;

means for advancing an overtube of the tool to position a shield of the tool over the inwardly bent spikes; and means for withdrawing the tool and the prosthesis from the esophagus.

* * * * *